United States Patent [19]

DeMey, II

[11] 4,121,859
[45] Oct. 24, 1978

[54] PRESSURE TIGHT SEAL

[75] Inventor: Charles F. DeMey, II, West Redding, Conn.

[73] Assignee: The Perkin-Elmer Corporation, Norwalk, Conn.

[21] Appl. No.: 721,657

[22] Filed: Sep. 8, 1976

Related U.S. Application Data

[63] Continuation-in-part of Ser. No. 547,380, Feb. 6, 1975, abandoned.

[51] Int. Cl.² ............................................. F16L 35/00
[52] U.S. Cl. ...................................... 285/93; 285/328; 285/368; 285/375; 285/DIG. 18
[58] Field of Search ....... 285/328, 363, 368, DIG. 18, 285/405, 93, 412, 279, 268, DIG. 12, 375; 356/181, 246

[56] References Cited

U.S. PATENT DOCUMENTS

| | | | |
|---|---|---|---|
| 448,765 | 3/1891 | Kaiser | 285/363 X |
| 1,475,867 | 11/1923 | Peterson | 285/405 X |
| 1,595,310 | 8/1926 | Mueller et al. | 285/328 X |
| 1,791,810 | 2/1931 | Furman | 285/328 X |
| 2,567,062 | 9/1951 | Edelen | 285/328 X |
| 2,926,937 | 4/1960 | Parsons | 285/DIG. 18 |
| 3,214,201 | 10/1965 | Fonda | 285/363 |
| 3,258,281 | 6/1966 | Scott et al. | 285/328 |
| 3,284,112 | 11/1966 | Martin | 285/328 |
| 3,481,633 | 12/1969 | Schonholzer | 285/363 X |
| 3,989,285 | 11/1976 | Yancey | 285/363 X |

Primary Examiner—Dave W. Arola
Attorney, Agent, or Firm—Salvatore A. Giarratana; Francis L. Masselle; John D. Crane

[57] ABSTRACT

A seal between the opposing surfaces of two joined members, wherein at least one of the surfaces is disposed about a bore or cavity. A salient portion (edge or bead) is formed on at least one of the surfaces and around the bore or cavity, and a gasket of resilient material is disposed between the surfaces to overlay the salient portion. The portions of the opposing surfaces other than the salient portion are substantially planar, and the gasket extends across the salient portion. Each salient portion is preferably formed by its opposing surface being disposed at an incline to an apex and the gasket is configured to have a thickness such that some extending portion thereof aside the salient portion is subjected to compression, of lesser degree than that applied by being at the salient portion. Continual forces are applied through a spring means to clamp the members across the gasket in one embodiment, while the gasket is compressed within the bore or cavity to preclude voids at the sealing interface in another embodiment.

9 Claims, 5 Drawing Figures

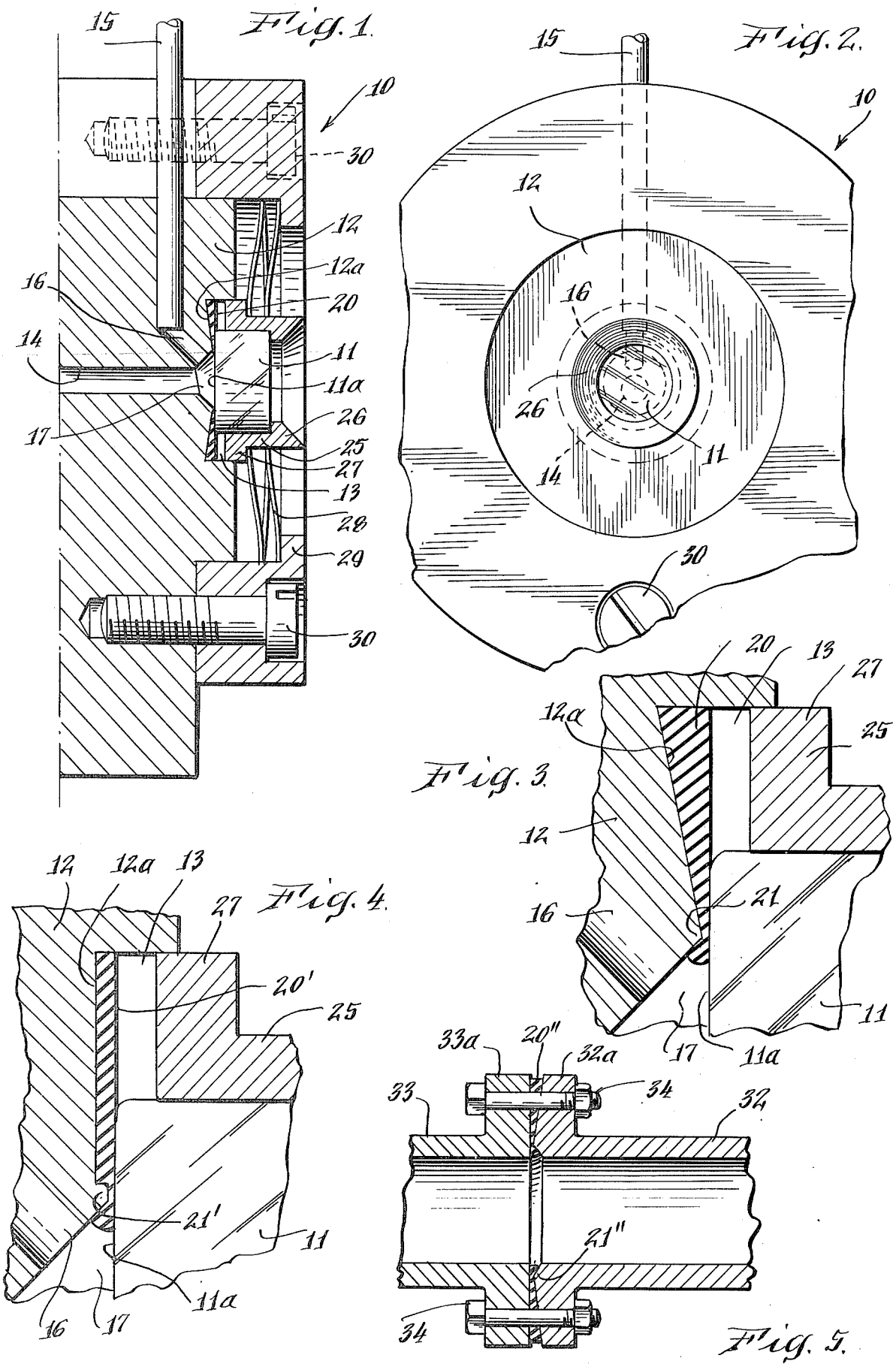

PRESSURE TIGHT SEAL

This is a continuation-in-part of application Ser. No. 547,380, filed Feb. 6, 1975.

BACKGROUND OF THE INVENTION

The present invention relates to a high pressure seal between joined members and particularly, to providing such a seal with a resilient gasket which is either continually compressed by a spring means or compressed within a bore or cavity to preclude voids at the sealing interface.

The seal of this invention has particular advantages for use in liquid chromatography detector cells for sealing the end windows which cover the cell chamber, as illustrated by the liquid chromatography (L.C.) detector cell assembly described in copending U.S. patent application Ser. No. 547,758 filed Feb. 6, 1975. Therefore this seal is described herein with reference to its use in such a cell. It will be appreciated, however, that the seal structure of this invention is also adaptable for use in other applications such as between abutting flanges of pipe joints.

High pressure seals known in the art customarily utilize elastomeric "O" rings or deformable metal parts as the gasket element. However, the grooves and face surfaces which cooperate with such gaskets to provide effective pressure tight seals must be accurately machined to very close tolerances so that these seals are somewhat expensive. Moreover, these seals, and other conventional sealing arrangements, are apt to prevent voids at the sealing interface in which gas bubbles or liquids tend to become trapped. In many applications, such entrapment is not a problem, but in analytical instrumentation such entrapment is a major consideration. A liquid chromatograph is one such instrument wherein samples are tested for traces of particular materials and wherein the conduits and interiors of detector cells must be rinsed clean of sample material before the introduction of a new test sample. Such cleaning is necessary because any residue of previous test material will contaminate successive samples to some extent and could severely reduce or completely destroy the usefulness of successive readings.

It is, therefore, the objects of the present invention to provide a continual high pressure, leak proof seal that is economical and to providing a sealing structure such that interfacing voids at which gas bubbles or liquid could become trapped are eliminated.

BRIEF SUMMARY OF THE INVENTION

In accordance with the present invention, a seal at the opposing surfaces of a joint, such as the joint between a window and the body of an L.C. detector cell or the flanges of a pipe joint, includes a salient portion, which may be an edge or a bead, on at least one of the opposing surfaces and extending around the bore or cavity that is in one or both faces. The opposing face portions other than from the salient portion on the opposing surfaces are planar and a gasket of resilient material is placed between the opposing surfaces to overlay the salient portion in extending thereacross. A spring means is incorporated in one embodiment so that when the joint is assembled with the opposing surfaces brought together to compress the gasket the sealing pressure is continual and concentrated at the relatively small area of the salient portion. The salient portion is, of course, the apex of the opposing surface on which it is formed with the remaining portions of that surface being of lesser height. Therefore, the thickness and resiliency of the gasket, are predetermined to provide that portions thereof disposed aside the salient portion are subjected to sufficient compression in preventing the gasket from migrating relative to the salient portion. In a particular embodiment, the bore or cavity is countersunk and the gasket is compressed therein to preclude voids at the sealing interface.

DESCRIPTION OF THE DRAWINGS

The foregoing and further objects, advantages and features of the present invention will be apparent from the subsequent description of the illustrative embodiments shown in the accompanying drawings in which:

FIG. 1 is a sectional view through part of a detector cell for liquid chromatography incorporating a seal embodying the invention, FIG. 2 is a side elevation looking at the right hand side of the cell shown in FIG. 1;

FIG. 3 is an enlarged sectional view through a portion of the seal in the cell shown in FIG. 1;

FIG. 4 is a sectional view, generally similar to the view of FIG. 3, but illustrating another embodiment of the seal of this invention; and FIG. 5 is a sectional view through a flanged pipe joint incorporating still another seal embodiment of this invention.

DETAILED DESCRIPTION

FIGS. 1–3 illustrate the seal of this invention as used in a detector cell 10 of a liquid chromatograph. The seal is between the face surface 11a of a clear quartz window 11 and surface 12a in a body 12 of the detector cell 10 at the bottom of a cylindrical recess 13. The chamber of the cell 10 is formed by a bore 14 through the body 12 at the bottom of the recess 13. The other side (not shown) of the detector cell 10 has a window similar to 11 over the other end of the bore 14, and sealed in similar fashion.

In operation of the detector cell 10 a sample to be analyzed is fed through the bore 14 from an inlet conduit 15, through a passage 16 into a lead or an enlarged end portion 17 of the bore 14 at the window 11, and thence through the bore 14 and out through an outlet passage and conduit (not shown) at the other end of the bore 14. In liquid chromatography, detection of a particular material in a sample passing through the bore 14 is determined by directing a beam of radiation having a particular wavelength therethrough between the end windows and applying instrumentation to determine the amount of the radiation that is absorbed.

The seal accomplished with this invention is best seen in the enlarged view of FIG. 3. It includes a gasket 20 of resilient material, such as polytetrafluoroethylene, compressed between the surfaces 11a and 12a. In practice, a seal constructed in accordance with this invention and withstanding an internal pressure of over 2,500 p.s.i. was made using polytetrafluoroethylene material on the order of 0.004 inch (0.1mm) thick. Surface 12a is provided with a salient portion 21 which projects therefrom and extends around the circumference of the lead 17 at the end of the bore 14. As shown in FIG. 3 where the salient portion 21 is an edge formed by inclining the bottom of the recess 13 toward an apex near surface 11a. In the embodiment shown in FIG. 4 the comparable salient portion 21' is a bead which presents an apex near surface 11a and around the circumference of the lead 17 with the bottom of the recess 13 otherwise being flat on a level lower than the apex. In both instances, and in accordance with the invention, the salient portions 21, 21' are provided between the opposing surfaces 11a and 12a within the joint so that the greatest compression of the gasket 20 therein will be at the salient 21, 21' when the opposing face surfaces 11a and 12a are brought together under compression.

The gaskets 20, 20' are relatively thin in comparison with their width and, in the assembly of the joint are placed to overlay the salient portions 21, 21' and extend thereacross. Portions of the gaskets 20, 20' disposed aside the salient portions 21, 21' are sufficiently compressed to prevent the gasket material from creeping in the joint so that the integrity of the seal is maintained. For salient portions of predetermined configurations, this is accomplished by selecting the resiliency and thickness or cross sectional configuration of the gasket 20 or 20' so that the portion thereof aside the salient portion 21, or 21' will be under compression of a relatively lesser degree but will thereby serve to stabilize the joint by inhibiting any rocking motion of the window 11 about the salient portion 21, or 21'. In practice a suitable seal constructed in the manner illustrated in FIG. 3 was made using a gasket of polytetrafluoroethylene 0.004 inch (0.1mm) thick with the surface 12a being inclined to diverage at an angle of about 3° relative to surface 11a.

In the detector cell 10 shown in FIGS. 1 to 3, the window 11 is held to the body portion 12 under compression, with the gasket 20 therebetween. This is accomplished by a bushing 25 that fits around and retains the window 11 with an inwardly extending flange 26 at one end while having an outwardly extending flange 27 at the other end thereof fitting slideably into the recess 13 of the cell body 12. In one embodiment the gasket 20 is placed in the recess 13 followed by the window 11 and bushing 25, with a number, suitably 3, of Belleville washers 28 being compressed against the flange 27 of the bushing 25. The washers 28 are held under compression against the flange 27 by a flanged retaining ring 29 tightened down on the body 12 of the cell by screws 30.

In the embodiments of the invention as described up to this point the salient portions 21, 21' are on only one of the opposing surfaces of the joint. It will be appreciated, however, that concentrated compression of the gasket 20 or 20' which is a critical factor to the invention, could also be provided by having salient portions formed on both opposing surfaces at corresponding locations and in exact alignment so that they come together against the gasket 20 or 20' from opposite sides when the joint is assembled.

In the embodiments shown in FIGS. 1–4 the salient portions 21, 21' are at the outer circumference of the lead 17 at the end of the bore 14. The lead 17 is a chamferred surface suitably formed by countersinking the end of the bore, 14 and is provided as a means to enhance a smooth flow of a fluid sample into the bore 14. The fluid enters through the passage 16 into the lead 17, washes against the window 11 and is thereby deflected into the bore 14. This construction is not necessary or critical to the seal of this invention; the lead 17 could be a counterbore so that the end of the bore 14 and the surface 12a would be at right angles or nearly so. However, the chamferred or counter-sunk end of the bore 14 provides a particular embodiment of the invention because an acute angle between the end of the bore 14 and the face surface 11a of the window 11 results therefrom so that the gasket 20 is compressed within the bore 14 to fill the sealing interface, and thereby voids in which liquid or gas could become trapped are precluded.

FIG. 5 illustrates the embodiment of this invention, wherein voids are precluded at the sealing interface but in a flange joint between two sections of pipe 32 and 33, wherein the flanges 32a and 33a are held together by throughbolts 34. As shown, the opposing surface on flange 32a is inclined toward its inward edge to form a salient portion or bead 21'', and a gasket 20'' is under compression between the opposing surfaces with a portion thereof being under maximum compression at the salient 21'' and with another portion thereof being compressed between the countersunk surface on pipe 32 and the opposing surface on pipe 33 to fill the sealing interface.

What is claimed is:

1. A seal between opposing surfaces of two joined members where one said joined member has a surface disposed around a cavity opening and the other joined member has no cavity opening, the seal comprising, in combination:
    a projecting portion disposed on the opposed surface around said cavity opening which projects therefrom in a direction toward the other joined member, said projecting portion forming a ring around said cavity opening comprising the points of farthest projection toward the other member;
    a gasket of resilient material disposed between said opposing surfaces to overlay said ring and at least a portion of said projecting portion on either side of said ring;
    a retainer member attached by attachment means to the joined member having a cavity opening;
    pressure exerting means comprising a spring member disposed between said retainer member and the joined member without a cavity opening, said pressure exerting means for urging the other joined member toward said gasket to produce substantially uniform compression of said gasket adjacent said ring;
    said projecting portion being shaped cooperatively with said joined member without a cavity opening to provide maximum compression of said gasket of said gasket between said ring and the other joined member and compression of a lesser degree between said other joined member and points on the joined member with a cavity opening both radially outward and radially inward of said ring.

2. The seal of claim 1 wherein at least one of said opposing surfaces is inclined toward an apex located in proximity to said other opposing surface, said apex forming said ring.

3. The seal of claim 1 wherein one joined member is made of a light transmitting material and is shaped to completely overlay said cavity opening.

4. The seal of claim 1 wherein said spring means comprises a stack of annular disc springs engaged against said joined member without a cavity and said retainer member, said attachment means for compressing said annular disc springs between said joined member without a cavity and said retainer member.

5. The seal of claim 4 wherein said outwardly projecting portion is on the order of 1 mm wide and said gasket is a ring of polytetrafluoroethylene on the order of 0.1 mm thick when not compressed.

6. A seal between opposing surfaces of two joined members wherein one said joined member has a surface disposed around a cavity opening and the other joined member has no cavity opening, the seal comprising, in combination:

a projecting portion disposed around the cavity opening of the joined member having such cavity opening, said projecting portion projecting in a direction toward the other joined member, said projecting portion forming a continuous ring around said cavity opening at the points of farthest projection toward said other joined member, the opposing surface of the other joined member without a cavity comprising a substantially planar surface;

a gasket of resilient material disposed to overlay said ring and at least a portion of said opposed surface radially outward of said ring around said cavity opening, said gasket being disposed between said opposing surfaces;

a retainer member attached by attachment means to said joint member with a cavity opening;

spring means disposed between said retainer member and said other joined member to urge said other joined member toward said gasket to produce substantially uniform compression of said gasket between said ring and said other joined member, said other joined member and said joined member with a cavity opening being cooperatively shaped to produce compression of said gasket of a lesser degree at points located radially outward of said ring.

7. The seal of claim 6 wherein said surface radially outward of said ring is disposed substantially at a three degree angle in the radial direction to the plane of the opposing surface of said other joined member.

8. The seal of claim 6 wherein said other other joined member is made of a light transmitting material permitting light to be directed through said cavity opening from an external light source.

9. The seal of claim 6 wherein said spring means comprises at least one disk spring.

* * * * *